United States Patent

Eicken et al.

Patent Number: 6,147,104
Date of Patent: Nov. 14, 2000

[54] FLUOROPYRAZOLE-BIPHENYLAMIDE FUNGICIDES

[75] Inventors: Karl Eicken, Wachenheim; Michael Rack, Heidelberg; Frank Wetterich, Mutterstadt; Eberhard Ammermann, Heppenheim; Gisela Lorenz, Neustadt; Siegfried Strathmann, Limburgerhof, all of Germany

[73] Assignee: BASF Aktiengesellschaft, Ludwigshafen, Germany

[21] Appl. No.: 09/485,403

[22] PCT Filed: Jul. 25, 1998

[86] PCT No.: PCT/EP98/04663

§ 371 Date: Feb. 10, 2000

§ 102(e) Date: Feb. 10, 2000

[87] PCT Pub. No.: WO99/09013

PCT Pub. Date: Feb. 25, 1999

[30] Foreign Application Priority Data

Aug. 15, 1997 [DE] Germany .............. 197 35 224

[51] Int. Cl.$^7$ .......... A01N 43/56; C07D 231/14
[52] U.S. Cl. .......... 514/406; 548/374.1
[58] Field of Search .......... 548/374.1; 514/406

[56] References Cited

U.S. PATENT DOCUMENTS

| | | |
|---|---|---|
| 4,001,416 | 1/1977 | Pommer et al. . |
| 5,438,070 | 8/1995 | Eicken et al. . |
| 5,480,897 | 1/1996 | Eicken et al. . |
| 5,675,016 | 10/1997 | Gallenkamp et al. . |

FOREIGN PATENT DOCUMENTS

| | | |
|---|---|---|
| 276 177 | 7/1988 | European Pat. Off. . |
| 545 099 | 6/1993 | European Pat. Off. . |
| 589 301 | 3/1994 | European Pat. Off. . |
| 776 889 | 6/1997 | European Pat. Off. . |
| 24 17 216 | 11/1975 | Germany . |

OTHER PUBLICATIONS

Elbe et al, *Chem Abstracts*, vol. 132, No. 180571, abstract of WO 2000014071, 2000.
Patent Abst. JP, vol. 12, No. 263 Abst. JP. 97/034280/03 (1997).

*Primary Examiner*—Robert W. Ramsuer
*Attorney, Agent, or Firm*—Keil & Weinkauf

[57] ABSTRACT

The invention relates to biphenylamides having general formula (I), and their salts, in which $R^1$ is H or F; $R^2$ is H, halogen, alkyl, halogen methyl, alkoxy, alkylthio; $R^3$ is $CH_3$, $CHF_2$, $CF_3$. The invention also relates to agents containing biphenylamnides, the production of biphenylamides and their use in combating parasitic fungus.

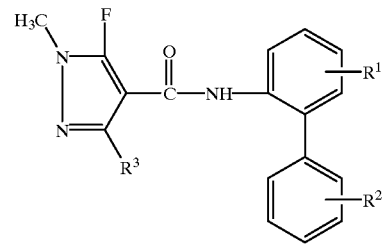

5 Claims, No Drawings

FLUOROPYRAZOLE-BIPHENYLAMIDE FUNGICIDES

This application is a 371 of PCT/EP98/0466B filed Jul. 25, 1998.

The present invention relates to a biphenyl amide of the formula I

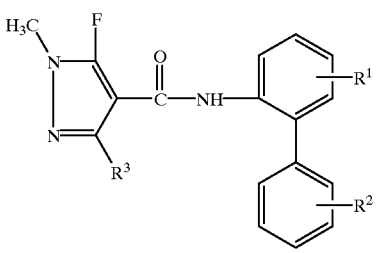

and salts thereof, where the radicals $R^1$, $R^2$ and $R^3$ have the following meanings:

$R^1$ is hydrogen or fluorine;

$R^2$ is hydrogen, halogen, $C_1$–$C_4$-alkyl, halomethyl, in particular fluoro- or chloromethyl such as, for example, trifluoromethyl, trichloromethyl, $C_1$–$C_4$-alkoxy or $C_1$–$C_4$-alkylthio;

$R^3$ is methyl, difluoromethyl or trifluoromethyl.

Additionally, the invention relates to a process for preparing the compounds I, to compositions comprising I and to a method for controlling harmful fungi and to the use of the compounds I, their salts or the compositions for this purpose.

Fungicidal biphenylamides of type I are disclosed in the following publications: U.S. Pat. No. 5,438,070, DE-A 24 17 216, EP-A 545 099 and EP-A 589 301. However, the active compounds mentioned in these publications are not satisfactory with respect to their activity.

It is an object of the present invention to provide biphenylamides having better activity against harmful fungi.

We have found that this object is achieved by the compounds I defined at the outset.

Furthermore, we have found compositions comprising the compounds I or salts thereof and a process for preparing I and the compositions. Moreover, we have found a method for controlling harmful fungi, and the use of the compounds I, their salts or the compositions for this purpose.

The compounds I are obtainable in a manner known per se from the corresponding acyl halides II and the biphenylamines III with the aid of a base such as, for example, triethanolamine.

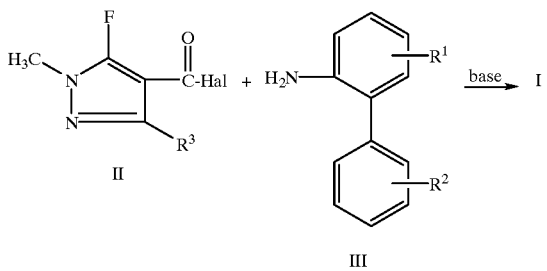

Hal is halogen, preferably chlorine or bromine;
$R^1$ is hydrogen or fluorine;
$R^2$ is hydrogen, halogen, $C_1$–$C_4$-alkyl, halomethyl, in particular fluoro- or chloromethyl such as, for example, trifluoromethyl, trichloromethyl, $C_1$–$C_4$-alkoxy or $C_1$–$C_4$-alkylthio;

$R^3$ is methyl, difluoromethyl or trifluoromethyl.

For the reaction conditions for preparing the compounds I and for the origin of the starting materials II, cf. for example Wo 93/11117, pages 17–19.

The biphenylamines III are generally known or obtainable in a manner known per se (cf. for example Tetrahedron Letters 28 (1987), 5093–5096).

The salts of the acid-stable compounds I which contain basic centers, especially basic nitrogen atoms, and in particular with salts of mineral acids such as sulfuric acid and phosphoric acid or Lewis acids such as zinc chloride also form part of the subject matter of the present invention. Generally, the kind of salt does not matter. For the purposes of the invention, preference is given to those salts which do not damage the plants, areas, materials or spaces to be kept free from harmful fungi and which do not adversely affect the activity of the compounds I. Particularly important are salts of this kind which are suitable for agricultural purposes.

The salts of the compounds I are obtainable in a manner known per se, especially by reacting the corresponding biphenylamides I with the abovementioned acids in water or an inert organic solvent at temperatures from –80 to 120° C., preferably from 0 to 60° C.

In the definitions of the compounds I to III given at the outset, collective terms were used which are representative of the following substituents:

halogen: fluorine, chlorine, bromine and iodine;

alkyl: straight-chain or branched alkyl groups having 1 to 4 carbon atoms, for example $C_1$–$C_4$-alkyl such as methyl, ethyl, n-propyl, 1-methylethyl, n-butyl, 1-methylpropyl, 2-methylpropyl, 1,1-dimethylethyl, 1-methylbutyl, 2-methylbutyl, 3-methylbutyl;

alkoxy: straight-chain or branched alkoxy groups having 1 to 4 carbon atoms, for example $C_1$–$C_3$-alkoxy such as methyloxy, ethyloxy, propyloxy and 1-methylethyloxy;

alkylthio: straight-chain or branched alkyl groups having 1 to 4 carbon atoms (as mentioned above) which are linked to the skeleton via a sulfur atom (—S—), for example methylthio, ethylthio, propylthio, 1-methylethylthio, n-butylthio and tert-butylthio.

With respect to their biological activity against harmful fungi, preference is given to compounds I in which $R^2$ is halogen, in particular fluorine, chlorine or bromine;

$C_1$–$C_4$-alkyl, in particular methyl, ethyl, propyl, 1-methylethyl, butyl, 1-methylpropyl, 2-methylpropyl or 1,1-dimethylethyl;

$C_1$–$C_4$-alkoxy, in particular methoxy, ethoxy, propoxy, 1-methylethoxy, butoxy, 1-methylpropoxy, 2-methylpropoxy or 1,1-dimethylethoxy;

alkylthio, in particular methylthio, ethylthio, n-propylthio or isopropylthio.

With respect to their use for controlling harmful fungi, very particular preference is given to the compounds I compiled in Table 1 below.

TABLE 1

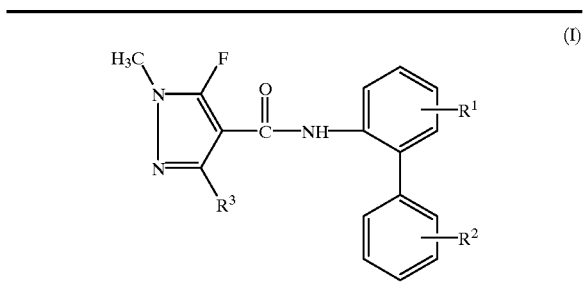

(I)

| No. | R¹ | R² | R³ |
|---|---|---|---|
| 1.1 | H | H | $CH_3$ |
| 1.2 | H | 3'-$CH_3$ | $CH_3$ |
| 1.3 | H | 3'-F | $CH_3$ |
| 1.4 | H | 3'-Cl | $CH_3$ |
| 1.5 | H | 3'-$CH_3$ | $CH_3$ |
| 1.6 | H | 3'-$OCH_3$ | $CH_3$ |
| 1.7 | H | 3'-$OCH(CH_3)_2$ | $CH_3$ |
| 1.8 | H | 3'-Br | $CH_3$ |
| 1.9 | H | 4'-F | $CH_3$ |
| 1.10 | H | 4'-Cl | $CH_3$ |
| 1.11 | H | 4'-$CH_3$ | $CH_3$ |
| 1.12 | H | 4'-$OCH_3$ | $CH_3$ |
| 1.13 | H | 4'-$SCH_3$ | $CH_3$ |
| 1.14 | H | 4'-$CF_3$ | $CH_3$ |
| 1.15 | 4-F | H | $CH_3$ |
| 1.16 | 4-F | 3'-$CH_3$ | $CH_3$ |
| 1.17 | 4-F | 3'-F | $CH_3$ |
| 1.18 | 4-F | 3'-Cl | $CH_3$ |
| 1.19 | 4-F | 3'-$CH_3$ | $CH_3$ |
| 1.20 | 4-F | 3'-$OCH_3$ | $CH_3$ |
| 1.21 | 4-F | 3'-$OCH(CH_3)_2$ | $CH_3$ |
| 1.22 | 4-F | 3'-Br | $CH_3$ |
| 1.23 | 4-F | 4'-F | $CH_3$ |
| 1.24 | 4-F | 4'-Cl | $CH_3$ |
| 1.25 | 4-F | 4'-$CH_3$ | $CH_3$ |
| 1.26 | 4-F | 4'-$OCH_3$ | $CH_3$ |
| 1.27 | 4-F | 4'-$SCH_3$ | $CH_3$ |
| 1.28 | 4-F | 4'-$CF_3$ | $CH_3$ |
| 1.29 | 5-F | H | $CH_3$ |
| 1.30 | 5-F | 3'-F | $CH_3$ |
| 1.31 | 5-F | 3'-Cl | $CH_3$ |
| 1.32 | 5-F | 3'-$CH_3$ | $CH_3$ |
| 1.33 | 5-F | 3'-$OCH_3$ | $CH_3$ |
| 1.34 | 5-F | 3'-$OCH(CH_3)_2$ | $CH_3$ |
| 1.35 | 5-F | 3'-Br | $CH_3$ |
| 1.36 | 5-F | 4'-$SCH_3$ | $CH_3$ |
| 1.37 | 5-F | 4'-$OCH_3$ | $CH_3$ |
| 1.38 | 5-F | 4'-$CF_3$ | $CH_3$ |
| 1.39 | 6-F | H | $CH_3$ |
| 1.40 | 6-F | 3'-F | $CH_3$ |
| 1.41 | 6-F | 3'-Cl | $CH_3$ |
| 1.42 | 6-F | 3'-$CH_3$ | $CH_3$ |
| 1.43 | 6-F | 3'-$OCH_3$ | $CH_3$ |
| 1.44 | 6-F | 3'-$OCH(CH_3)_2$ | $CH_3$ |
| 1.45 | 6-F | 3'-Br | $CH_3$ |
| 1.46 | 6-F | 4'-F | $CH_3$ |
| 1.47 | 6-F | 4'-Cl | $CH_3$ |
| 1.48 | 6-F | 4'-$CH_3$ | $CH_3$ |
| 1.49 | 6-F | 4'-$OCH_3$ | $CH_3$ |
| 1.50 | 6-F | 4'-$SCH_3$ | $CH_3$ |
| 1.51 | 6-F | 4'-$CF_3$ | $CH_3$ |
| 1.52 | H | H | $CF_3$ |
| 1.53 | H | 3'-F | $CF_3$ |
| 1.54 | H | 3'-Cl | $CF_3$ |
| 1.55 | H | 3'-$CH_3$ | $CF_3$ |
| 1.56 | H | 3'-$OCH_3$ | $CF_3$ |
| 1.57 | H | 3'-$OCH(CH_3)_2$ | $CF_3$ |
| 1.58 | H | 3'-Br | $CF_3$ |
| 1.59 | H | 4'-F | $CF_3$ |
| 1.60 | H | 4'-Cl | $CF_3$ |
| 1.61 | H | 4'-$CH_3$ | $CF_3$ |
| 1.62 | H | 4'-$OCH_3$ | $CF_3$ |
| 1.63 | H | 4'-$SCH_3$ | $CF_3$ |
| 1.64 | H | 4'-$CF_3$ | $CF_3$ |
| 1.65 | 4-F | H | $CF_3$ |
| 1.66 | 4-F | 3'-F | $CF_3$ |
| 1.67 | 4-F | 3'-Cl | $CF_3$ |
| 1.68 | 4-F | 3'-$CH_3$ | $CF_3$ |
| 1.69 | 4-F | 3'-$OCH_3$ | $CF_3$ |
| 1.70 | 4-F | 3'-$OCH(CH_3)_2$ | $CF_3$ |
| 1.71 | 4-F | 3'-Br | $CF_3$ |
| 1.72 | 4-F | 4'-F | $CF_3$ |
| 1.73 | 4-F | 4'-Cl | $CF_3$ |
| 1.74 | 4-F | 4'-$CH_3$ | $CF_3$ |
| 1.75 | 4-F | 4'-$OCH_3$ | $CF_3$ |
| 1.76 | 4-F | 4'-$SCH_3$ | $CF_3$ |
| 1.77 | 4-F | 4'-$CF_3$ | $CF_3$ |
| 1.78 | 5-F | H | $CF_3$ |
| 1.79 | 5-F | 3'-F | $CF_3$ |
| 1.80 | 5-F | 3'-Cl | $CF_3$ |
| 1.81 | 5-F | 3'-$CH_3$ | $CF_3$ |
| 1.82 | 5-F | 3'-$OCH_3$ | $CF_3$ |
| 1.83 | 5-F | 3'-$OCH(CH_3)_2$ | $CF_3$ |
| 1.84 | 5-F | 3'-Br | $CF_3$ |
| 1.85 | 5-F | 4'-$OCH_3$ | $CF_3$ |
| 1.86 | 5-F | 4'-$SCH_3$ | $CF_3$ |
| 1.87 | 5-F | 4'-$CF_3$ | $CF_3$ |
| 1.88 | 6-F | H | $CF_3$ |
| 1.89 | 6-F | 3'-F | $CF_3$ |
| 1.90 | 6-F | 3'-Cl | $CF_3$ |
| 1.91 | 6-F | 3'-$CH_3$ | $CF_3$ |
| 1.92 | 6-F | 3'-$OCH_3$ | $CF_3$ |
| 1.93 | 6-F | 3'-$OCH(CH_3)_2$ | $CF_3$ |
| 1.94 | 6-F | 3'-Br | $CF_3$ |
| 1.95 | 6-F | 4'-F | $CF_3$ |
| 1.96 | 6-F | 4'-Cl | $CF_3$ |
| 1.97 | 6-F | 4'-$CH_3$ | $CF_3$ |
| 1.98 | 6-F | 4'-$OCH_3$ | $CF_3$ |
| 1.99 | 6-F | 4'-$SCH_3$ | $CF_3$ |
| 1.100 | 6-F | 4'-$CF_3$ | $CF_3$ |

The fungicidally active compounds I and their salts can be applied for example in the form of ready-to-spray solutions, powders or suspensions or in the form of highly concentrated aqueous, oily or other suspensions or dispersions, emulsions, oil dispersions, pastes, dusts, materials for scattering or granules, by spraying, atomizing, dusting, scattering or watering. The use form depends on the intended purpose; in any case, it should guarantee as fine a distribution as possible of the active compounds according to the invention.

Usually, the plants are sprayed or dusted with the active compounds, or the seeds of the plants are treated with the active compounds.

The formulations are prepared using customary formulation auxiliaries—as described below—and in a manner known per se, for example by extending the active compound with solvents and/or carriers, if desired by using emulsifiers and dispersants. If the diluent used is water, other, organic solvents can be used as auxiliary solvents. Suitable auxiliaries are essentially: solvents, such as aromatics (for example xylene), chlorinated aromatics (for example chlorobenzenes), paraffins (for example petroleum fractions), alcohols (for example methanol, butanol), ketones (for example cyclohexanone), amines (for example ethanolamine, dimethylformamide) and water; carriers, such as ground natural minerals (for example kaolins, clays, talc, chalk) and synthetic ground minerals (for example finely divided silica, silicates); emulsifiers, such as nonionic and anionic emulsifiers (for example polyoxyethylene fatty alcohol ethers, alkylsulfonates and arylsulfonates) and dispersants, such as lignosulfite waste liquors and methylcellulose.

Suitable surfactants are the alkali metal salts, alkaline earth metal salts and ammonium salts of aromatic sulfonic acids, for example ligno-, phenol-, naphthalene- and dibutylnaphthalenesulfonic acid, and of fatty acids, alkylsulfonates and alkylarylsulfonates, alkyl sulfates, lauryl ether sulfates and fatty alcohol sulfates, and salts of sulfated hexa-, hepta- and octadecanols, or of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenol or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors or methylcellulose.

Powders, materials for scattering and dusts can be prepared by mixing or jointly grinding the active compounds with a solid carrier.

Granules, for example coated granules, impregnated granules or homogeneous granules, can be prepared by binding the active compounds to solid carriers. Solid carriers are mineral earths such as silica gel, silicas, silica gels [sic], silicates, talc, kaolin, limestone, lime, chalk, bole, loess, clay, dolomite, diatomaceous earth, calcium sulfate, magnesium sulfate, magnesium oxide, ground synthetic materials, and fertilizers, such as ammonium sulfate, ammonium phosphate, ammonium nitrate, ureas and products of vegetable origin, such as cereal meal, tree bark meal, wood meal and nutshell meal, cellulose powders or other solid carriers.

Examples of such preparations are:

I. a solution of 90 parts by weight of a compound I according to the invention and 10 parts by weight of N-methyl-2-pyrrolidone, which is suitable for use in the form of microdrops;

II. a mixture of 10 parts by weight of a compound I according to the invention, 70 parts by weight of xylene, 10 parts by weight of the adduct of 8 to 10 mol of ethylene oxide to 1 mol of oleic acid N-monoethanolamide, 5 parts by weight of calcium dodecylbenzenesulfonate, 5 parts by weight of the adduct of 40 mol of ethylene oxide to 1 mol of castor oil; a dispersion is obtained by finely distributing the solution in water;

III. an aqueous dispersion of 10 parts by weight of a compound I according to the invention, 40 parts by weight of cyclohexanone, 30 parts by weight of isobutanol, 20 parts by weight of the adduct of 40 mol of ethylene oxide to 1 mol of castor oil;

IV. an aqueous dispersion of 10 parts by weight of a compound I according to the invention, 25 parts by weight of cyclohexanol, 55 parts by weight of a petroleum fraction of boiling point 210 to 280° C. and 10 parts by weight of the adduct of 40 mol of ethylene oxide to 1 mol of castor oil;

V. a mixture, ground in a hammer mill, of 80 parts by weight of a compound I according to the invention, preferably in solid form, 3 parts by weight of sodium diisobutylnaphthalene-2-sulfonate, 10 parts by weight of the sodium salt of a lignosulfonic acid from a sulfite waste liquor and 7 parts by weight of pulverulent silica gel; a spray mixture is obtained by finely distributing the mixture in water;

VI. an intimate mixture of 3 parts by weight of a compound I according to the invention and 97 parts by weight of finely divided kaolin; this dust comprises 3% by weight of active compound;

VII. an intimate mixture of 30 parts by weight of a compound I according to the invention, 62 parts by weight of pulverulent silica gel and 8 parts by weight of paraffin oil which has been sprayed onto the surface of this silica gel; this formulation imparts good adhesion to the active compound;

VIII. a stable aqueous dispersion of 40 parts by weight of a compound I according to the invention, 10 parts by weight of the sodium salt of a phenolsulfonic acid/urea/ formaldehyde condensate, 2 parts by weight of silica gel and 48 parts by weight of water, it being possible for this dispersion to be diluted further;

IX. a stable oily dispersion of 20 parts by weight of a compound I according to the invention, 2 parts by weight of calcium dodecylbenzenesulfonate, 8 parts by weight of fatty alcohol polyglycol ether, 20 parts by weight of the sodium salt of a phenolsulfonic acid/urea/formaldehyde condensate and 50 parts by weight of a paraffinic mineral oil.

The novel compounds have an outstanding activity against a broad range of phytopathogenic fungi, in particular from the classes of the Deuteromycetes, Ascomycetes, Phycomycetes and Basidiomycetes. Some of them act systemically and can be employed as foliar- and soil-acting fungicides.

They are especially important for controlling a large number of fungi in a variety of crops, such as wheat, rye, barley, oats, rice, maize, lawns, cotton, soy, coffee, sugar cane, grapevines, fruit species, ornamentals and vegetable species such as cucumbers, beans and cucurbits as well as the seeds of these plants.

The compounds are applied by treating the fungi, their habitat or the plants, areas or materials to be kept free from them with an effective amount of the active compounds.

Application is effected before or after infection of the materials, plants or seeds by the fungi.

Specifically, the novel compounds are suitable for controlling the following plant diseases:

*Erysiphe graminis* (powdery mildew) in cereals, *Erysiphe cichoracearum* and *Sphaerotheca fuliginea* in cucurbits, *Podosphaera leucotricha* in apples, *Uncinula necator* in grapevines, Puccinia species in cereals, Rhizoctonia species in cotton and lawns, Ustilago species in cereals and sugar cane, *Venturia inaequalis* (scab) in apples, Helminthosporium species in cereals, *Septoria nodorum* in wheat, *Botrytis cinerea* (gray mold) in strawberries, grapevines, ornamentals and vegetables, Monilinia species in fruit, *Cercospora arachidicola* in groundnuts, *Pseudocercosporella herpotrichoides* in wheat and barley, *Pyricularia oryzae* in rice, *Phytophthora infestans* in potatoes and tomatoes, Fusarium and Verticillium species in a variety of plants, *Plasmopara viticola* in grapevines, Alternaria species in vegetables and fruit.

In general, the fungicidal compositions comprise from 0.1 to 95, preferably from 0.5 to 90, % by weight of active compound.

Depending on the nature of the desired effect, the rates of application are from 0.025 to 2, preferably from 0.1 to 1, kg, of active compound per ha.

In the treatment of seed, amounts of from 0.001 to 50 g, preferably 0.01 to 10 g, of active compound are generally required per kilogram of seed.

The novel compounds can also be used in the protection of materials (wood protection), for example against *Paecilomyces variotii*.

The compositions according to the invention in the use form as fungicides may also be present together with other active compounds, eg. with herbicides, insecticides, growth regulators, fungicides or else with fertilizers.

In many cases, a mixture with fungicides results in a widened fungicidal spectrum of action.

The following list of fungicides together with which the compounds according to the invention can be used is intended to illustrate the possible combinations, but not to impose any limitation:

sulfur, dithiocarbamates and their derivatives, such as iron dimethyldithiocarbamate, zinc dimethyldithiocarbamate, zinc ethylenebisdithiocarbamate, manganese ethylenebisdithiocarbamate, manganese zinc ethylenediamine-bis-dithiocarbamate, tetramethylthiuram disulfide, ammonia complex of zinc (N,N-ethylene-bis-dithiocarbamate), ammonia complex of zinc (N,N'-propylene-bis-dithiocarbamate), zinc (N,N'-propylene-bisdithiocarbamate), N,N'-polypropylenebis(thiocarbamoyl) disulfide;

nitro derivatives, such as dinitro-(1-methylheptyl)phenyl crotonate, 2-sec-butyl-4,6-dinitrophenyl-3,3-dimethyl acrylate, 2-sec-butyl-4,6-dinitrophenylisopropyl carbonate, diisopropyl 5-nitroisophthalate;

heterocyclic substances, such as 2-heptadecyl-2-imidazoline acetate, 2,4-dichloro-6-(o-chloroanilino)-s-triazine, 0,0-diethyl phthalimidophosphonothioate, 5-amino-1-[bis(dimethylamino)-phosphinyl]-3-phenyl-1,2,4-triazole, 2,3-dicyano-1,4-dithio-anthraquinone, 2-thio-1,3-dithiolo[4,5-b]quinoxaline, methyl 1-(butylcarbamoyl)-2-benzimidazolecarbamate, 2-methoxycarbonyl-aminobenzimidazole, 2-(furyl-(2))benzimidazole, 2-(thiazolyl-(4))benzimidazole, N-(1,1,2,2-tetrachloroethylthio)tetrahydrophthalimide, N-trichloromethylthiotetrahydrophthalimide, N-trichloromethylthiophthalimide, N-dichlorofluoromethylthio-N',N'-dimethyl-N-phenylsulfuric diamide, 5-ethoxy-3-trichloromethyl-1,2,3-thiadiazole, 2-thiocyanatomethylthiobenzothiazole, 1,4-dichloro-2,5-dimethoxy-benzene, 4-(2-chlorophenylhydrazono)-3-methyl-5-isoxazolone, pyridine-2-thione 1-oxide, 8-hydroxyquinoline or its copper salt, 2,3-dihydro-5-carboxanilido-6-methyl-1,4-oxathiine, 2,3-dihydro-5-carboxanilido-6-methyl-1,4-oxathiine 4,4-dioxide, 2-methyl-5,6-dihydro-4H-pyran-3-carboxanilide, 2-methylfuran-3-carbox-anilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine 2,2,2-trichloroethyl acetal, piperazine-1,4-diylbis-1-(2,2,2-trichloroethyl)formamide, 1-(3,4-dichloroanilino)-1-formylamino-2,2,2-trichloroethane, 2,6-dimethyl-N-tridecyl-morpholine or its salts, 2,6-dimethyl-N-cyclododecylmorpholine or its salts, N-[3-(p-tert-butylphenyl)-2-methylpropyl]-cis-2,6-dimethylmorpholine, N-[3-(p-tert-butylphenyl)-2-methyl-propyl]piperidine, 1-[2-(2,4-dichlorophenyl)-4-ethyl-1,3-dioxolan-2-ylethyl]-1H-1,2,4-triazole, 1-[2-(2,4-dichlorophenyl)-4-n-propyl-1,3-dioxolan-2-ylethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, (2-chlorophenyl)-(4-chlorophenyl)-5-pyrimidine-methanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)-benzene, [2-(4-chlorophenyl)ethyl]-(1,1-dimethylethyl)-1H-1,2,4-triazole-1-ethanol, 1-[3-(2-chlorophenyl)-1-(4-fluorophenyl)-oxiran-2-ylmethyl]-1H-1,2,4-triazole, and a variety of fungicides, such as dodecylguanidine acetate, 3-[3-(3,5-dimethyl-2-oxycyclohexyl)-2-hydroxyethyl] glutarimide, hexachlorobenzene, methyl N-(2,6-dimethylphenyl)-N-(2-furoyl)-DL-alaninate, DL-N-(2,6-dimethylphenyl)-N-(2'-methoxyacetyl)-alanine methyl ester, N-(2,6-dimethylphenyl)-N-chloroacetyl-D,L-2-aminobutyrolactone, DL-N-(2,6-dimethylphenyl)-N-(phenyl-acetyl)alanine methyl ester, 5-methyl-5-vinyl-3-(3,5-dichloro-phenyl)-2,4-dioxo-1,3-oxazolidine, 3-(3,5-dichlorophenyl)-5-methyl-5-methoxymethyl-1,3-oxazolidine-2,4-dione, 3-(3,5-dichlorophenyl)-1-iso-propylcarbamoylhydantoin, N-(3,5-dichlorophenyl)-1,2-dimethylcyclopropane-1,2-dicarboximide, 2-cyano-[N-(ethylaminocarbonyl)-2-methoximino]-acetamide, 1-[2-(2,4-dichlorophenyl)pentyl]-1H-1,2,4-triazole, 2,4-difluoro-α-(1H-1,2,4-triazolyl-1-methyl)benzhydryl alcohol, N-(3-chloro-2,6-dinitro-4-trifluoromethylphenyl)-5-trifluoromethyl-3-chloro-2-aminopyridine, 1-((bis-(4-fluorophenyl)methyl-silyl) methyl)-1H-1,2,4-triazole, strobilurins, such as methyl E-methoximino-[α-(o-tolyloxy)-o-tolyl]acetate, methyl E-2-{2-[6-(2-cyanophenoxy)pyridimin-4-yl-oxy]phenyl}-3-methoxyacrylate, N-methyl-E-methoximino-α-(2,5-dimethyloxy [sic])-o-tolyl)acetamide.

Anilinopyrimidines, such as N-(4,6-dimethylpyrimidin-2-yl)-aniline, N-[4-methyl-6-(1-propynyl)pyrimidin-2-yl] aniline, N-(4-methyl-6-cyclopropylpyrimidin-2-yl)aniline.

Phenylpyrroles, such as 4-(2,2-difluoro-1,3-benzodioxol-4-yl)-pyrrole-3-carbonitrile.

Cinnamamides, such as 3-(4-chlorophenyl)-3-(3,4-dimethoxyphenyl)-acryloylmorpholide.

Synthesis examples

The procedures for preparing the compounds I and III given in the synthesis examples below can be used to obtain further representatives of the formula I or III by modification of the starting materials. Some of the physical data of the products prepared in this manner are also given in the Tables 2 and 3 which follow.

EXAMPLE 1

(intermediate of type III)

2-Amino-5,41-difluorobiphenyl (no. 2.3 in Table 2)

Under nitrogen, 2.4 g of tetrakis(triphenylphosphine) palladium, 15.1 g (0.108 mol) of 4-fluorophenylboronic acid and a solution of 30 g (0.282 mol) of sodium carbonate in 120 ml of water was added to a solution of 11.4 g (0.060 mol) of 2-bromo-4-fluoroaniline in 120 ml of 1,2-dimethoxyethane, and the mixture was heated under reflux for 8 hours. After cooling, 200 ml of methyl tert-butyl ether and 100 ml of water were added. The organic phase was washed with water, dried and concentrated. Chromatography of the residue over 50 g of silica gel using cyclohexane as eluent gave 12.4 g of the title compound (m.p.: 67–69° C.).

TABLE 2

(III)

![structure III]

| No. | R¹ | R² | M.p. [° C.] |
|---|---|---|---|
| 2.1 | 5-F | H | Oil |
| 2.2 | 5-F | 4'-Cl | 75–80 |
| 2.3 | 5-F | 4'-F | 67–69 |
| 2.4 | 5-F | 4'-CH₃ | 73–76 |
| 2.5 | 3-F | H | |
| 2.6 | 3-F | 4'-Cl | |
| 2.7 | 3-F | 4'-F | |
| 2.8 | 3-F | 4'-CH₃ | |
| 2.9 | 4-F | H | |
| 2.10 * | 4-F | 4'-F | |
| 2.11 | 4-F | 4'-Cl | |
| 2.12 | 4-F | 4'-CH₃ | |
| 2.13 | 6-F | H | |
| 2.14 | 6-F | 4'-F | |
| 2.15 | 6-F | 4'-Cl | |
| 2.16 | 6-F | 4'-CH₃ | |

* Alternative synthesis: reduction of the corresponding nitro compound (cf. Chem. Ber. 64 (1931), p. 1332 ff.; J. Chem. Soc. (1930), p. 1159 ff.; Chem. Ber. 61 (1928), p. 1407 ff.)

EXAMPLE 2

(active compound of type I)

N-(4'-chlorobiphenyl)-1,3-dimethyl-5-fluoropyrazole-4-carboxamide

At +5° C., a solution of 1.15 g (7 mmol) of 1,3-dimethyl-5-fluoropyrazole-4-carbonyl chloride in 3 ml of tetrahydrofuran was added dropwise to a solution of 1.42 g (7 mmol) of 2-amino-4'-chlorobiphenyl and 0.71 g (7 mmol) of triethylamine in 7 ml of tetrahydrofuran, and the mixture was then stirred for 20 minutes at +5° C. and for 2 hours at room temperature. The mixture was stirred into 140 ml of water and the precipitated was filtered off by suction. Digestion with a mixture of diisopropyl ether and cyclohexane (1:2) gave 1.5 g of the title compound (m.p.: 146–150° C., no. 1.10 in the table below).

TABLE

[lacuna]

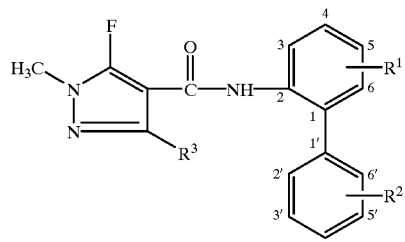

(I)

| No. | R¹ | R² | R³ | M.p. [° C.] |
|---|---|---|---|---|
| 1.1 | H | H | CH₃ | 147–150 |
| 1.9 | H | 4'-F | CH₃ | 138–139 |
| 1.10 | H | 4'-Cl | CH₃ | 135–139 |
| 1.11 | H | 4'-CH₃ | CH₃ | 113–114 |
| 1.59 | H | 4'-F | CF₃ | — |
| 1.60 | H | 4'-Cl | CF₃ | — |
| 1.61 | H | 4'-CH₃ | CF₃ | — |

Use examples

The following tests on the fungicidal activity of the compounds I were carried out using an emulsion comprising 10% by weight of the active compound and 90% by weight of a mixture of

| | |
|---|---|
| 70% by weight of | cyclohexanol, |
| 20% by weight of | Nekanil ® LN (Lutensol ® AP6, wetting agent having emulsifying and dispersing action based on ethoxylated alkylphenols) and |
| 10% by weight of | Emulphor ® EL (Emulan ® EL, emulsifier based on ethoxylated fatty alcohols). |

The desired active compound concentrations were obtained by diluting this emulsion with water.

2'-Ethyl-2-chloronicotinanilide served as comparative compound "A", 2'-phenyl-2-chloronicotinanilide served as comparative compound "B". Both compounds are disclosed in DE-A-24 17 216.

Use example 1

*Botrytis cinerea*

Disks of green bell pepper fruits were sprayed to run-off with an aqueous preparation which had been prepared according to the above procedure and comprised in each case 250 ppm of a single active compound. The active compound used was the compound 1.10 according to the invention.

2 hours after the spray coating had dried on, the fruit disks were inoculated with a spore suspension of the fungus *Botrytis cinerea* containing 1.7×10⁶ spores per ml of a 2% strength Biomalz solution. The fruit disks were subsequently incubated for 4 days at 18° C. in chambers of high atmospheric humidity.

Visual scoring showed a fungal infection of 0–15% of the disk surfaces for the abovementioned compound.

In the case of compound "A", the fungal infection, under otherwise identical test conditions, was 100%.

Disks which had not been treated with a compound I or with the compound "A" showed 100% infection.

Use example 2

*Erysiphe graminis* var. tritici

Leaves of wheat seedlings (cv. "Frühgold") which had been grown in pots were sprayed with an aqueous preparation which had been prepared according to the above procedure and comprised in each case 250 ppm of a single active compound. The active compound used was the compound 1.10 according to the invention.

24 hours after the spray coating had dried on, the leaves were dusted with oidia (spores) of wheat mildew (*Erysiphe graminis* var. tritici). The plants were subsequently incubated for 7 days at 20–22° C. and a relative atmospheric humidity of 75–80%.

Visual scoring showed a fungal infection of 5–25% of the leaf surface for the abovementioned compound.

In the case of the compound "A", the fungal infection, under otherwise identical test conditions, was 60%. An infection of 80% was determined for "B". Leaves which had not been treated with a compound I, "A" or "B" showed 80% infection.

We claim:

1. A biphenyl amide of the formula I

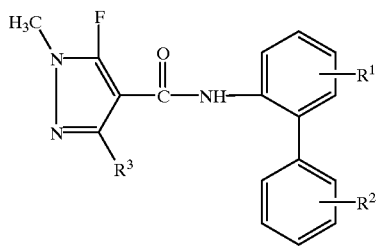

and salts thereof, where the radicals $R^1$, $R^2$ and $R^3$ have the following meanings:

$R^1$ is hydrogen or fluorine;

$R^2$ is hydrogen, halogen, $C_1$–$C_4$-alkyl, halomethyl, $C_1$–$C_4$-alkoxy or $C_1$–$C_4$-alkylthio;

$R^3$ is methyl, difluoromethyl or trifluoromethyl.

2. A process for preparing biphenyl amides of the formula I as claimed in claim 1, which comprises reacting an acyl halide of the formula II

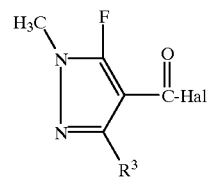

in which Hal is halogen, with a biphenylamine of the formula III

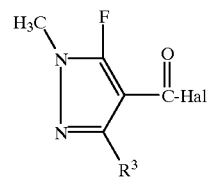

with the aid of a base.

3. A composition suitable for controlling harmful fungi, which comprises an effective amount of at least one compound of the formula I or a salt thereof as claimed in claim 1 and at least one customary formulation auxiliary.

4. A process for preparing the composition as claimed in claim 3, which comprises jointly processing, in a manner known per se, a fungicidally effective amount of at least one compound of the formula I or a salt thereof as with at least one customary formulation auxiliary.

5. A method for controlling harmful fungi, which comprises treating the harmful fungi, their habitat or the plants, spaces, areas or materials to be kept free from them with an effective amount of at least one compound of the formula I or a salt thereof or with a composition comprising I or a salt thereof as claimed in claim 3.

* * * * *